(12) United States Patent
Bonde-Larsen et al.

(10) Patent No.: US 10,040,765 B2
(45) Date of Patent: *Aug. 7, 2018

(54) METHODS FOR THE PREPARATION OF INDACATEROL AND PHARMACEUTICALLY ACCEPTABLE SALTS THEREOF

(71) Applicant: Crystal Pharma S.A.U., Valladolid (ES)

(72) Inventors: Antonio Lorente Bonde-Larsen, Valladolid (ES); Yolanda Fernández Sainz, Valladolid (ES); Jesús Iglesias Retuerto, Valladolid (ES); Javier Gallo Nieto, Valladolid (ES)

(73) Assignee: Crystal Pharma S.A.U., Valladolid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/278,945

(22) Filed: Sep. 28, 2016

(65) Prior Publication Data

US 2017/0015628 A1 Jan. 19, 2017

Related U.S. Application Data

(62) Division of application No. 14/427,568, filed as application No. PCT/EP2013/068618 on Sep. 9, 2013, now Pat. No. 9,475,772.

(30) Foreign Application Priority Data

Sep. 21, 2012 (EP) .................. PCT/EP2012/003961

(51) Int. Cl.
| | | |
|---|---|---|
| C07D 215/227 | (2006.01) |
| C07D 215/26 | (2006.01) |
| C07C 51/41 | (2006.01) |
| C07C 57/145 | (2006.01) |
| C07C 59/255 | (2006.01) |

(52) U.S. Cl.
CPC .......... *C07D 215/227* (2013.01); *C07C 51/41* (2013.01); *C07C 57/145* (2013.01); *C07C 59/255* (2013.01); *C07D 215/26* (2013.01); *C07B 2200/13* (2013.01)

(58) Field of Classification Search
CPC .. C07D 215/227; C07D 215/26; C07C 51/41; C07C 57/145; C07C 59/255; C07B 2200/13

See application file for complete search history.

(56) References Cited

U.S. PATENT DOCUMENTS

| | | | |
|---|---|---|---|
| 6,653,323 B2 | 11/2003 | Moran et al. | |
| 7,622,483 B2 | 11/2009 | Cuenoud et al. | |
| 9,475,772 B2 * | 10/2016 | Bonde-Larsen | ..... C07D 215/26 |
| 2004/0038951 A1 | 2/2004 | Cuenoud et al. | |

FOREIGN PATENT DOCUMENTS

| | | |
|---|---|---|
| JP | 2006-517978 A | 8/2006 |
| JP | 2008-542319 A | 11/2008 |
| JP | 2009-529042 A | 8/2009 |
| JP | 2010-519195 A | 6/2010 |
| WO | WO 00/075114 A1 | 12/2000 |
| WO | WO 2004/016578 A2 | 2/2004 |
| WO | WO 2004/074246 A2 | 9/2004 |
| WO | WO 2004/076422 A1 | 9/2004 |
| WO | WO 2006/128675 A1 | 12/2006 |
| WO | WO 2007/057221 A2 | 5/2007 |
| WO | WO 2007/102771 A1 | 9/2007 |
| WO | WO 2007/124898 A1 | 11/2007 |
| WO | WO 2008/102128 A2 | 8/2008 |

OTHER PUBLICATIONS

International Search Report for PCT/EP2013/068618 dated Dec. 6, 2013.

* cited by examiner

*Primary Examiner* — D Margaret M Seaman
(74) *Attorney, Agent, or Firm* — Knobbe Martens Olson & Bear LLP

(57) ABSTRACT

The invention relates to new and improved processes for the preparation of Indacaterol and pharmaceutically acceptable salts thereof as well as intermediates for the preparation of Indacaterol. The new process avoids the use of the epoxide compound known in the art and the impurities associated therewith and results in a higher yield.

1 Claim, No Drawings

METHODS FOR THE PREPARATION OF INDACATEROL AND PHARMACEUTICALLY ACCEPTABLE SALTS THEREOF

CROSS REFERENCE TO RELATED APPLICATIONS

This application is a divisional of and claims the benefit and priority to U.S. patent application Ser. No. 14/427,568, filed on Mar. 11, 2015, which is a U.S. National Phase application of PCT International Application Number PCT/EP2013/068618, filed on Sep. 9, 2013, designating the United States of America and published in the English language, which is an International Application of and claims the benefit of priority to International Patent Application No. PCT/EP2012/003961, filed on Sep. 21, 2012. The disclosures of the above-referenced applications are hereby expressly incorporated by reference in their entireties.

FIELD OF THE INVENTION

The present invention relates to new and improved processes for the preparation of Indacaterol and pharmaceutically acceptable salts thereof as well as intermediates for the preparation of Indacaterol.

BACKGROUND OF THE INVENTION

The compound 5-[(R)-2-(5,6-diethyl-indan-2-ylamino)-1-hydroxyethyl]-8-hydroxy-(1H)-quinolin-2-one, which is known as Indacaterol (INN), and its corresponding salts are beta-selective adrenoceptor agonists with a potent bronchodilating activity. Indacaterol is especially useful for the treatment of asthma and chronic obstructive pulmonary disease (COPD) and is sold commercially as the maleate salt.

WO 00/75114 and WO 2004/076422 describe the preparation of Indacaterol for the first time through the process:

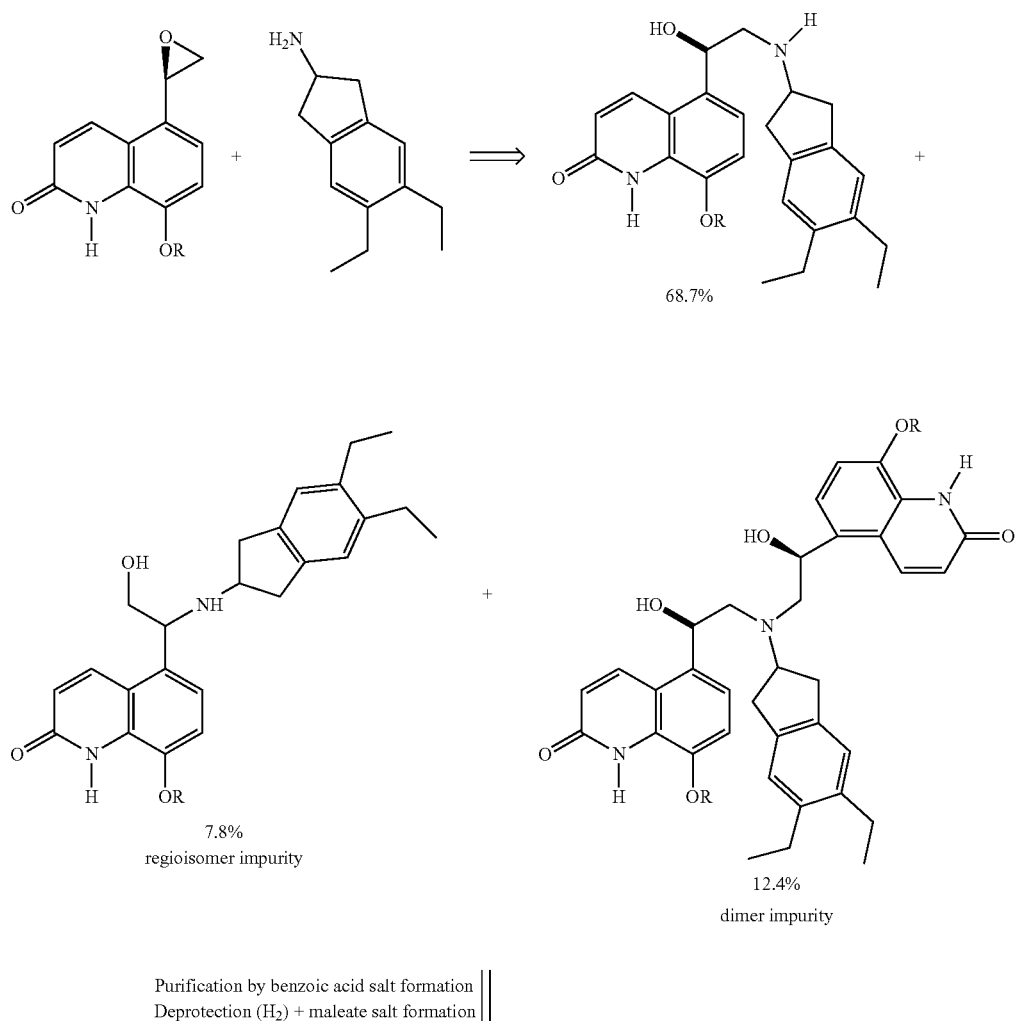

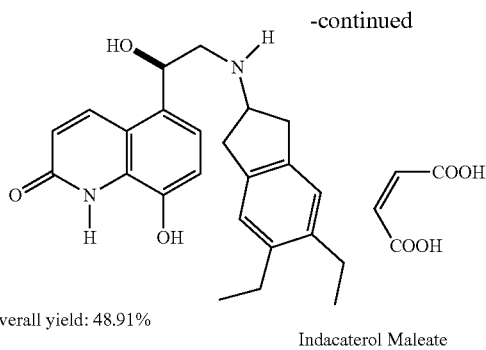

Overall yield: 48.91%

Indacaterol Maleate

The condensation between the indanolamine and the quinolone epoxide leads to the desired product but always with the presence of a significant amount of impurities, the most significant being the dimer impurity, which is the consequence of a second addition of the product initially obtained with another quinolone epoxide, as well as the formation of another isomer which is the result of the addition of the indanolamine to the secondary carbon of the epoxide.

In addition, the reaction conditions to achieve the opening of the epoxide require high energies (ex. 21 of WO 00/75114) with temperatures of 110° C. or more for several hours, which favours the appearance of impurities.

WO 2004/076422 discloses the purification of the reaction mixture by the initial formation of a salt with an acid, such as tartaric acid or benzoic acid, hydrogenation and final formation of the maleate salt. However, the yield achieved by the end of the process is only 49% overall.

It has been found that impurities of tartrate and benzoate salts can exist in the final product as a result of displacing the tartrate or benzoate with maleate without prior neutralization to Indacaterol base. In addition, WO 2004/076422 discloses that proceeding via the free base of Indacaterol is not viable due to its instability in organic solvents. WO 00/75114 does disclose a method proceeding via the Indacaterol free base, but it is not isolated in solid form.

WO 2004/076422 furthermore discloses the method for obtaining the quinolone epoxide from the corresponding α-haloacetyl compound by reduction in the presence of a chiral catalyst, such as an oxazaborolidine compound, by proceeding via the α-halohydroxy compound.

There exists, therefore, the need to develop an improved process for obtaining Indacaterol and salts thereof, which overcomes some or all of the problems associated with known methods from the state of the art. More particularly, there exists the need for a process for obtaining Indacaterol and pharmaceutically acceptable salts thereof, which results in a higher yield and/or having fewer impurities in the form of the dimer and regioisomers impurities and/or salts other than the desired pharmaceutically acceptable salt.

SUMMARY OF THE INVENTION

In one aspect of the invention, it concerns a process for preparing Indacaterol or a pharmaceutically acceptable salt thereof comprising reacting the compound of formula I with 2-amino-5,6-diethylindan of formula II, preferably in the presence of a base, to the compound of formula III and then converting the compound of formula III to Indacaterol or a pharmaceutically acceptable salt thereof:

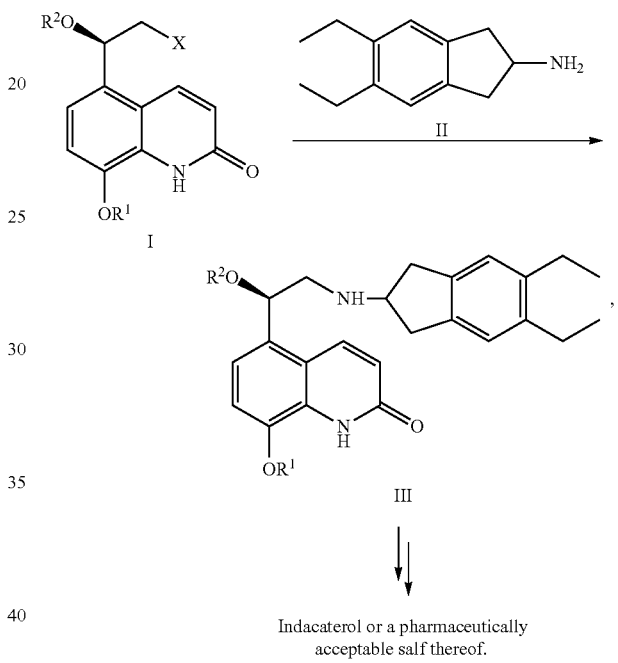

Indacaterol or a pharmaceutically
acceptable salt thereof.

wherein $R^1$ is a protecting group, $R^2$ is a protecting group, which is stable under mildly alkaline conditions, and X is a halogen selected from the group consisting of chloro, bromo, and iodo.

This process avoids the formation of the dimers and regiostereoisomers associated with the processes known in the art, e.g. in WO 2004/076422, since it avoids the use of the epoxy compound used in the prior art processes. This facilitates the purification of the compound of formula III, possible subsequent intermediates in the process, as well as the final product. The process of the invention furthermore has gentler reaction conditions than the processes known in the art and results in a yield of more than 70% and in some cases more than 80%.

$R^1$ is a protecting group commonly known in the art for protecting phenol groups. $R^2$ is a protecting group, which is stable under mildly alkaline conditions.

A further aspect of the invention concerns a process for the preparation of the compound of formula III or a salt thereof by reacting the compound of formula I with 2-amino-5,6-diethylindan of formula II to the compound of formula III. Optionally, the compound of formula III is converted to a salt thereof by addition of an acid.

In another aspect of the invention, it concerns a process for the preparation of a pharmaceutically acceptable salt of Indacaterol by obtaining Indacaterol, isolating it in solid form, and reacting it with a suitable acid, such as maleic acid.

Still another aspect of the invention concerns the compounds of formula I. Yet another aspect of the invention concerns the compounds of formula III. A further aspect of the invention concerns Indacaterol free base in solid form.

DETAILED DESCRIPTION OF THE INVENTION

Definitions

In the context of the present invention, the term "$C_{6-20}$ aryl" is intended to mean an optionally substituted fully or partially aromatic carbocyclic ring or ring system with 6 to 20 carbon atoms, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

In the context of the present invention, the term "$C_{1-6}$ alkyl" is intended to mean a linear or branched saturated hydrocarbon group having from one to six carbon atoms, such as methyl, ethyl, n-propyl, isopropyl, n-butyl, isobutyl, sec-butyl, tert-butyl, n-pentyl, isopentyl, neopentyl and n-hexyl.

In the context of the present invention, the term "$C_{1-6}$-alkoxy" is intended to mean $C_{1-6}$-alkyl-oxy, such as methoxy, ethoxy, n-propoxy, iso-propoxy, n-butoxy, iso-butoxy, sec-butoxy, tert-butoxy, n-pentoxy, iso-pentoxy, neo-pentoxy and n-hexoxy.

In the context of the present invention, the term "$C_{2-6}$ alkenyl" is intended to cover linear or branched hydrocarbon groups having 2 to 6 carbon atoms and comprising one unsaturated bond. Examples of alkenyl groups are vinyl, allyl, butenyl, pentenyl and hexenyl.

In the context of the present invention, the term "$C_{3-6}$ cycloalkyl" is intended to mean a cyclic hydrocarbon group having 3 to 6 carbon atoms, such as cyclopropyl, cyclobutyl, cyclopentyl and cyclohexyl.

In the context of the present invention, the term "heteroaryl" is intended to mean a fully or partially aromatic carbocyclic ring or ring system where one or more of the carbon atoms have been replaced with heteroatoms, e.g. nitrogen (=N— or —NH—), sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrimidinyl, pyrazinyl, pyridazinyl, triazinyl, coumaryl, furyl, thienyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl, phenoxazonyl, phenyl pyrrolyl and N-phenyl pyrrolyl.

In the present context, the term "optionally substituted" is intended to mean that the group in question may be substituted one or several times, preferably 1-3 times, with group(s) selected from hydroxy (which when bound to an unsaturated carbon atom may be present in the tautomeric keto form), $C_{1-6}$-alkoxy, $C_{2-6}$-alkenyloxy, carboxy, oxo (forming a keto or aldehyde functionality), $C_{1-6}$-alkoxycarbonyl, $C_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonyl amino, cyano, guanidino, carbamido, $C_{1-6}$-alkyl-sulphonyl-amino, arylsulphonyl-amino, heteroaryl-sulphonyl-amino, $C_{1-6}$-alkanoyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio and halogen.

In the present context, the term "mildly alkaline conditions" refers to conditions created when adding the compound of formula II, which is a base, to the compound of formula I, preferably in the presence of a further base, such as triethylamine, diisopropylethylamine (DIPEA), pyridine, 1,4-diazabicyclo[2.2.2]octane (DABCO), 4-dimethylaminopyridine (DMAP), sodium carbonate, potassium carbonate, sodium hydrogencarbonate, potassium hydrogencarbonate, sodium hydroxide, or potassium hydroxide.

Processes

In one aspect of the invention, it concerns a process for preparing Indacaterol or a pharmaceutically acceptable salt thereof comprising reacting the compound of formula I with 2-amino-5,6-diethylindan of formula II, preferably in the presence of a base, to the compound of formula III and then converting the compound of formula III to Indacaterol or a pharmaceutically acceptable salt thereof:

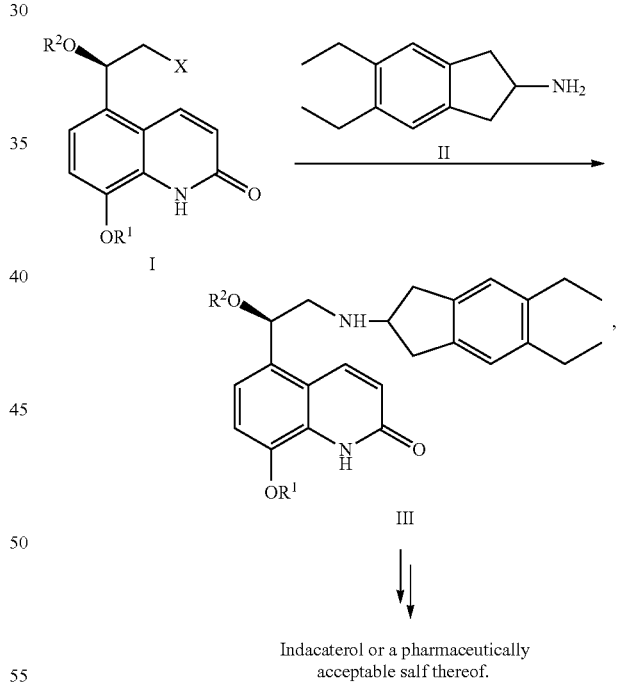

wherein $R^1$ is a protecting group, $R^2$ is a protecting group, which is stable under mildly alkaline conditions, and X is a halogen selected from the group consisting of chloro, bromo, and iodo.

In one embodiment, the compound of formula III is converted to Indacaterol by first converting it to a compound of formula IV by first removing the protecting group $R^2$ by addition of an acid, preferably an aqueous acid, and finally isolating/purifying the compound (IV) as a salt by adding the acid HA:

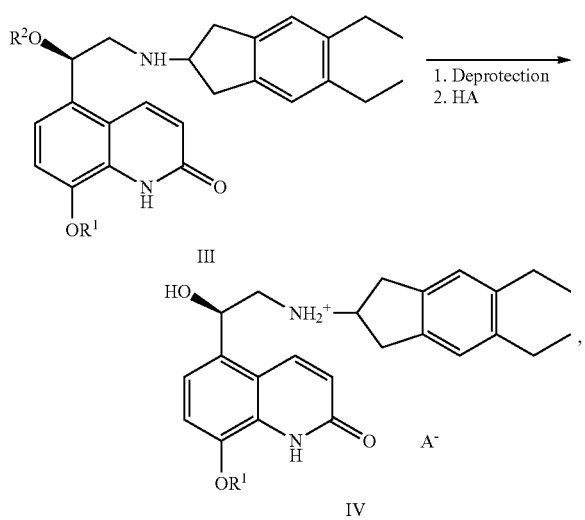

III

IV and then converting the compound of formula IV to Indacaterol or a pharmaceutically acceptable salt thereof. Processes for converting the compound of formula IV to Indacaterol or a pharmaceutically acceptable salt thereof are disclosed inter alia in WO 2004/076422.

In a further embodiment, the compound of formula IV is converted to Indacaterol or a pharmaceutically acceptable salt thereof by:
  a) neutralizing the compound of formula IV, removing the protecting group $R^1$ to obtain Indacaterol free base in solution or suspension, optionally isolating Indacaterol free base in solid form, and, optionally, obtaining a pharmaceutically acceptable salt of Indacaterol by addition of a suitable acid, such as maleic acid, to the free base;
  b) removing the protecting group $R^1$ to obtain a compound of formula V:

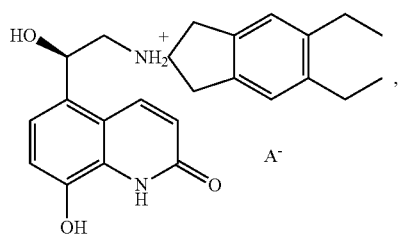

V neutralizing the compound of formula V to obtain the free Indacaterol base in solution or suspension, optionally isolating Indacaterol free base in solid form, and, optionally, obtaining a pharmaceutically acceptable salt of Indacaterol by addition of a suitable acid, such as maleic acid, to the free base; or
  c) removing the protecting group $R^1$ to obtain a compound of formula V, reacting the compound of formula V directly with a suitable acid, such as maleic acid, to obtain a pharmaceutically acceptable salt of Indacaterol.

The Compound of Formula III

The compound of formula III may be isolated as the free base or through the formation of an acid addition salt without removing the protecting group $R^2$ or used directly without isolating it in the further preparation of Indacaterol or a pharmaceutically acceptable salt thereof, such as proceeding via the compound of formula IV.

$R^1$ Protecting Groups $R^1$ is a protecting group commonly known in the art for protecting phenol groups. The skilled person will be aware of suitable protecting groups for hydroxy groups in the 8-position of quinolone derivatives such as the compound of formula I. Such suitable protecting groups may be found in WO 00/75114 and WO 2004/076422.

More particularly, in one embodiment, $R^1$ is selected from the group consisting of a $C_{1-6}$ alkyl, $C_{6-20}$ aryl, $C_{1-6}$-alkoxy, $C_{2-6}$ alkenyl, $C_{3-6}$ cycloalkyl, benzocycloalkyl, $C_{3-6}$ cycloalkyl-$C_{1-6}$ alkyl, $C_{6-20}$ aryl-$C_{1-6}$ alkyl, heteroaryl, heteroaryl-$C_{1-6}$ alkyl, halo-$C_{1-6}$ alkyl, and an optionally substituted silyl group. In another embodiment, $R^1$ is benzyl or t-butyldimethylsilyl. In yet another embodiment, $R^1$ is benzyl.

$R^2$ Protecting Groups $R^2$ is a protecting group, which is stable under mildly alkaline conditions and which can be cleaved off selectively under conditions where $R^1$ is not cleaved off. A number of protecting groups fulfil these criteria, including, but not limited to, protecting groups forming an acetal together with the adjacent oxygen atom, protecting groups forming an ether together with the adjacent oxygen, protecting groups forming a silyl ether group with the adjacent oxygen, and protecting groups forming an ester together with the adjacent oxygen. Hence, in one embodiment, $R^2$ forms an acetal, an ether, a silyl ether, or an ester together with the adjacent oxygen. In another embodiment, $R^2$ forms an acetal, an ether, or a silyl ether together with the adjacent oxygen. In yet another embodiment, $R^2$ forms an acetal or an ether together with the adjacent oxygen. In a further embodiment, $R^2$ forms an acetal together with the adjacent oxygen.

Examples of suitable acetal protecting groups are 1-(n-butoxy)-ethyl acetal and tetrahydro-pyran-2-yl acetal. Thus, in one embodiment, $R^2$ is 1-(n-butoxy)-ethyl or tetrahydro-pyran-2-yl, such as 1-(n-butoxy)-ethyl. Examples of suitable ether protecting groups are benzyl ether, methoxymethyl (MOM) ether, methylthiomethyl (MTM) ether, and benzyloxymethyl ether. Thus, in another embodiment, $R^2$ is benzyl, methoxymethyl, methylthiomethyl, or benzyloxymethyl, such as benzyl. Examples of suitable silyl ether protecting groups are trimethylsilyl ether and tert-butyldimethylsilyl ether. Thus, in still another embodiment, $R^2$ is trimethylsilyl or tert-butyldimethylsilyl. Examples of suitable ester protecting groups are pivaloyl ester and acetate ester. Thus, in yet another embodiment, $R^2$ is pivaloyl or acetate.

In a further embodiment, $R^2$ is selected from the group consisting of 1-(n-butoxy)-ethyl, methoxymethyl, benzyl, and tetrahydro-pyran-2-yl, such as from the group consisting of 1-(n-butoxy)-ethyl, methoxymethyl, and tetrahydro-pyran-2-yl. In yet a further embodiment, $R^2$ is 1-(n-butoxy)-ethyl and $R^1$ is benzyl.

Methods for Removing the Protecting Group $R^2$

The protecting group $R^2$ may be removed from the compound of formula III by methods known in the art for the various $R^2$ protecting groups defined herein. In the case of $R^2$ forming an acetal together with the adjacent oxygen atom, $R^2$ may be removed by reacting with an intermediate to strong acid, preferably in the presence of water. Examples of suitable acids are hydrochloric acid, hydrobromic acid, sulfuric acid, nitric acid, phosphoric acid, camphorsulfonic acid, methanesulfonic acid, trifluoromethanesulfonic acid, and combinations thereof.

In the case of $R^2$ forming an ether, silyl ether, or ester together with the adjacent oxygen atom, the acids mentioned for the acetal protecting groups are also suitable for removing $R^2$. Other suitable agents for removing $R^2$ in the case of $R^2$ forming an ether, silyl ether, or ester together with the adjacent oxygen atom are aqueous bases, lewis acids, hydrogen over palladium or platinum catalyst (in the case of benzyl ether), resins such as Dowex, thiols such as thiophenol, and combinations thereof.

Bases Useful in the Reaction of Compounds I and II

Any organic or inorganic base may be employed in the reaction between compounds I and II in the formation of the compound of formula III, with the exception of primary and secondary amines. Examples of useful organic bases in this reaction are triethylamine, diisopropylethylamine (DIPEA), pyridine, 1,4-diazabicyclo[2.2.2]octane (DABCO), and 4-dimethylaminopyridine (DMAP). Examples of useful inorganic bases in this reaction are sodium carbonate, potassium carbonate, sodium hydrogencarbonate, potassium hydrogencarbonate, sodium hydroxide, and potassium hydroxide. When carrying out the reaction between the compounds of formula I and II in the presence of a base, the 2-amino-5,6-diethylindan of formula II may be added to the reaction mixture in the form of an acid addition salt thereof, such as the hydrochloride salt thereof.

The Acid HA

Reacting the product obtained by removing the protecting group $R^2$ from the compound of formula III with the acid HA serves to purify the compound by obtaining the salt of formula IV. Examples of suitable HA acids are benzoic acid, maleic acid, fumaric acid, succinic acid, tartaric acid, hydrochloric acid, hydrobromic acid, dibenzoyl-tartaric acid, mandelic acid, and camphorsulfonic acid.

In one embodiment, the acid HA is selected from the group consisting of tartaric acid, dibenzoyl-tartaric acid, mandelic acid, succinic acid, and benzoic acid. In another embodiment, the acid HA is selected from the group consisting of tartaric acid, succinic acid, and benzoic acid.

The Halogen X

Halogens generally constitute good leaving groups in an $S_N2$-type reaction, such as the reaction between the compounds of formula I and II. In one embodiment, X is selected from the group consisting of chloro, bromo, and iodo. In another embodiment, X is bromo or iodo. In yet another embodiment, X is bromo.

In a further embodiment, X is bromo or chloro and the reaction between compounds I and II takes place in the presence of an iodine salt, such sodium iodide or potassium iodide, which generates the iodo group in situ.

The Starting Compound of Formula I

The compound of formula I may be obtained from the corresponding hydroxy-unprotected compound of formula VI:

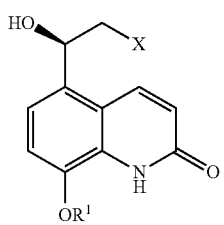

by reacting with the reagents known in the art to form the acetal, ether, silyl ether, or ester protecting groups defined herein when reacted with an alcohol. In the case of e.g. acetal protecting groups, in the case where $R^2$ is 1-(n-butoxy)-ethyl or tetrahydro-pyran-2-yl, the compound of formula VI may be reacted with butyl-vinyl ether or dihydro-pyran-2-yl, respectively.

The compound of formula VI may be prepared by reducing the corresponding haloacetyl compound using a chiral catalyst. Suitable chiral catalysts for this method are disclosed in WO 2004/076422 and WO 2005/123684, the contents of which are incorporated in their entirety herein.

Pharmaceutically Acceptable Salts

Pharmaceutically acceptable acid addition salts of Indacaterol are easily identified by the skilled person. A useful list of pharmaceutically acceptable acid addition salts may be found in Berge et al: "Pharmaceutical Salts", Journal of Pharmaceutical Sciences, vol. 66, no. 1, 1 Jan. 1977, pages 1-19. A particularly interesting pharmaceutically acceptable acid addition salt is the maleate salt.

Proceeding Via Indacaterol Base

As discussed above, Indacaterol free base is known in the art to be unstable in organic solvents. Hence, preparing pharmaceutically acceptable salts of Indacaterol by proceeding via the free Indacaterol base is not considered viable on an industrial scale. It has, however, been found that by isolating the free base in solid form, pharmaceutically acceptable salts of Indacaterol may indeed be prepared on an industrial scale by proceeding via the free Indacaterol base. Furthermore, this avoids the impurities associated with the methods known in the art for converting one salt of 8-protected Indacaterol directly to a pharmaceutically acceptable salt of Indacaterol. Example 2 of WO 2004/076422 was reproduced, hydrogenating the benzoate salt of formula IV using acetic acid as the solvent, and then exchanging the anion of the salt to maleate by addition of maleic acid. The obtained solid was filtered, washed, and dried in vacuum to give the Indacaterol maleate with impurities of Indacaterol acetate as measured by NMR (Comparative example 9).

Thus, in another aspect of the invention, it concerns a process for the preparation of a pharmaceutically acceptable salt of Indacaterol by obtaining Indacaterol, isolating it in solid form, and reacting it with a suitable acid, such as maleic acid. Indacaterol free base may be obtained as disclosed herein or as known in the art.

Useful Reaction Conditions

Formation of the Compound of Formula III

The reaction may take place in a number of different organic solvents. Useful examples are acetonitrile, butanone, and dimethylformamide (DMF), in particular acetonitrile and butanone. It has been found advantageous to use small volumes of solvent in the reaction between the compounds of formula I and II. The reaction is advantageously carried out at a temperature in the range of 70 to 110° C., such as at 85° C., with a duration of between 2 and 10 hours, such as 4 to 5 hours. Furthermore, when adding the 2-amino-5,6-diethylindan of formula II as an acid addition salt thereof, a carbonate salt, such as potassium carbonate, is advantageously added to the reaction mixture.

Removing the Protecting Group $R^2$

When using an aqueous acid for removing the protecting group $R^2$, e.g. 1-(n-butoxy)-ethyl, from the compound of formula III said acid, such as hydrochloric acid, is advantageously added in excess, such as 2 to 6 equivalents, at a temperature between room temperature and reflux until complete removal of the protecting group, e.g. 1 to 3 hours for removing the 1-(n-butoxy)-ethyl protecting group.

Formation of the Compound of Formula IV

Once the protecting group R² has been removed, more water may advantageously be added together with a suitable solvent, such as dichloromethane. The deprotected compound may be neutralized at a pH of 9 to 11 and the resulting phases then separated. After separation, the solvent may be changed to a solvent suitable for precipitation of the compound of formula IV. Useful solvents are ethyl acetate, isopropanol, ethanol, acetone, tetrahydrofuran, and acetonitrile, ethyl acetate, isopropanol, and ethanol currently being more preferred. After changing the solvent, the acid HA may be added to form the compound of formula IV by precipitation. Ethyl acetate is a particularly useful solvent for precipitating the benzoate, succinate, and tartrate salts. The salt of formula IV may be obtained with a yield of 65 to 80% and a purity of greater than 93%% in the case of tartrate precipitated in ethyl acetate, and a yield of 60 to 75% and a purity of greater than 99% in the case of succinate and tartrate precipitated in isopropanol or ethanol. The absence of dimer and regioisomer impurities as known in the art facilitates a more quantitative precipitation using ethyl acetate since there is no competition for the base molecules.

Formation of Indacaterol Base

The compound of formula IV may be neutralized before deprotection of R¹. The neutralization may suitably be achieved by addition of dichloromethane, water and soda. When R¹ is removed by hydrogenation, it may suitably be achieved using an overpressure of hydrogen at ambient temperature. Furthermore, a mixture of methanol and dichloromethane as the solvent is suitably employed in the process. Upon completion of the hydrogenation, the catalyst is removed and dichloromethane is distilled off to leave methanol as the only solvent, which causes Indacaterol to precipitate upon cooling. Alternatively, the methanol/dichloromethane mixture is exchanged with isopropanol solvent, which is cooled to achieve precipitation of Indacaterol base with a purity of >99%.

Precipitated Indacaterol base is a white solid, which may be stored at ambient temperature for extended periods of time. Upon dissolution it may be used to prepare a pharmaceutically acceptable salt, such as the maleate salt. A suitable solvent for the addition of maleic acid is isopropanol. Alternatively, Indacaterol base obtained from the reaction and dissolved in a mixture of methanol and dichloromethane can be used directly, the solvent exchanged for isopropanol, and then precipitated as the maleate salt by adding maleic acid.

Intermediate Compounds

The process of the invention involves novel intermediates, which have not previously been used in the preparation of Indacaterol. Hence, a further aspect of the invention concerns the compounds of formula I. Yet another aspect of the invention concerns the compounds of formula III, or salts thereof.

A further aspect of the invention concerns Indacaterol free base in solid form. In one embodiment, said Indacaterol free base is in crystalline form. In another embodiment, said Indacaterol free base is in amorphous form.

EXAMPLES

Example 1—Protecting the α-Halohydroxy Compound of Formula VI

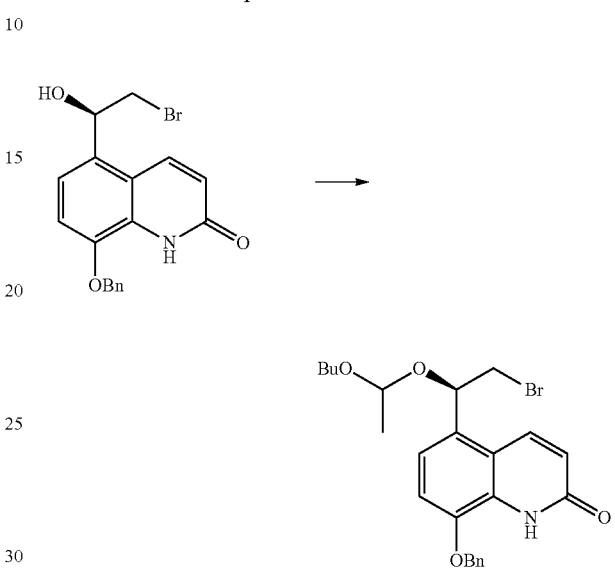

A flask was charged with 5 ml of tetrahydrofuran (THF) and 5 ml of toluene. p-toluene sulfonic acid (0.15 mmol) and molecular sieves were added with stirring for 30 minutes. 6 mmol of butyl-vinylether and 3 mmol of 8-(phenyl-methoxy)-5-((R)-2-bromo-1-hydroxy-ethyl)-(1H)-quinolin-2-one were added. The mixture was agitated at 20/25° C. until completion of the reaction, followed by filtration and distillation of the filtrate to remove the solvent. The product is obtained in quantitative yield as an oil consisting of 50% of each of the diastereomers.

¹H-NMR (DMSO-d6, δ), mixture 50/50 of diastereomers: 0.61 and 0.82 (3H, t, J=7.2 Hz, $CH_3$—Pr—O), 1.12 and 1.22 (3H, d, J=5.6 Hz, acetalic $CH_3$), 0.90-1.40 (4H, m, $CH_2$+$CH_2$), 3.20-3.80 (4H, m, $CH_2$—OAr+$CH_2$—Br), 4.51 and 4.82 (1H, q, J=5.6 Hz, acetalic CH), 5.18 and 5.24 (1H, dd, J=4.0, 8.0 Hz, CH—O-acetal), 6.56 and 6.58 (1H, d, J=10.0 Hz, H4), 7.00-7.57 (7H, m), 8.17 and 8.23 (1H, d, J=10.0 Hz, H3), 10.71 (1H, s, NH)

¹³C-NMR (DMSO-d6, δ), mixture 50/50 of diastereoisomers: 13.5 and 13.7 $CH_3$, 18.5 and 18.8 ($CH_2$), 19.9 and 20.0 (acetalic $CH_3$), 30.9 and 31.4 ($CH_2$), 36.8 and 37.3 ($CH_2$), 63.7 and 64.2 ($CH_2$—Br), 69.8 and 69.9 ($CH_2$—OAr), 73.8 and 75.1 (CH—O), 97.5 and 100.4 (acetalic CH), 111.8 (CH), 116.9 and 117.2 (C), 121.2 and 122.4 (CH), 122.3 and 122.6 (CH), 127.7 and 127.8 (C), 127.8 and 127.9 (CH), 128.2 and 128.3 (CH), 128.8 and 129.1 (C), 129.4 and 129.6 (C), 136.1 and 136.5 (CH), 136.5 and 136.6 (C), 144.0 and 144.2 (C), 160.7 and 160.8 (C=O).

Example 2—Protecting the α-Halohydroxy Compound of Formula VI

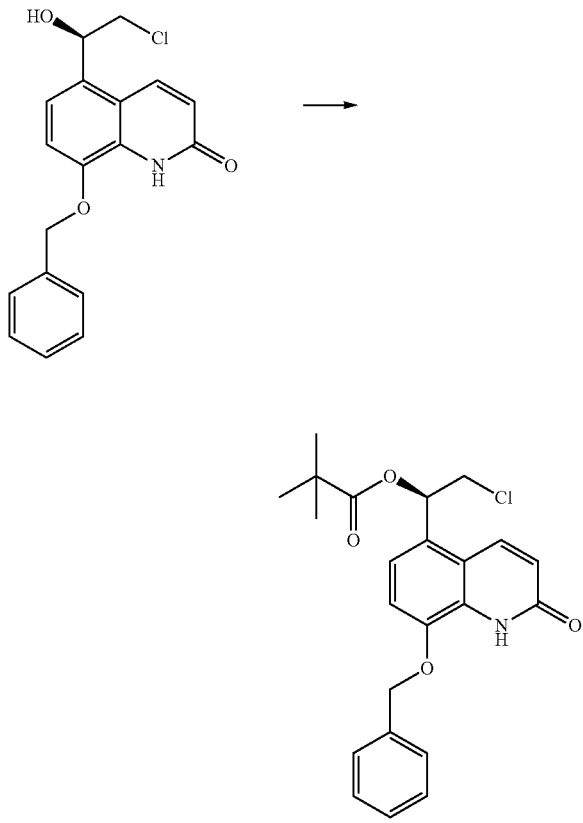

Pivaloyl chloride (0.72 g) was added to a stirred mixture of 8-(phenylmethoxy)-5-((R)-2-chloro-1-hydroxy-ethyl)-(1H)-quinolin-2-one (0.74 g), dichloromethane (15 ml) and 4-dimethylaminopyridine (0.89 g) at 20/25° C., and the reaction was stirred until all the starting material disappeared. Water (22 ml) was added and the phases were separated.

The organic phase was washed with 1 M HCl (22 ml) and then with water (22 ml). The solvent was removed and the residue was crystallized from acetone to obtain 0.82 g of the product.

$^1$H-NMR (DMSO-d6, δ): 1.13 (9H, s, CH$_3$), 3.92 (1H, dd, J=4.0, 12.0 Hz, CH$_2$—Br), 4.00 (1H, dd, J=8.4, 12.0 Hz, CH$_2$—Cl), 5.28 (2H, s, Ph-CH$_2$—O), 6.25 (1H, dd, J=4.0, 8.4 Hz, CH—OPiv), 6.59 (1H, d, J=10.0 Hz, H4), 7.15 (1H, d, J=8.4 Hz, H6), 7.20 (1H, d, J=8.4 Hz, H7), 7.27-7.30 (1H, m, Ph), 7.33-7.37 (2H, m, Ph), 7.54-7.56 (2H, m, Ph), 8.18 (1H, d, J=10.0 Hz, H3), 10.77 (1H, s, NH).

$^{13}$C-NMR (DMSO-d6, δ): 26.7 (3×CH$_3$), 38.3 (C), 46.4 (CH$_2$—Cl), 69.8 (CH$_2$-Ph), 71.3 (CH—OPiv), 111.9 (CH), 116.8 (C), 120.5 (CH), 122.9 (CH), 126.0 (C), 127.8 (2×CH), 127.9 (CH), 128.3 (2×CH), 129.5 (C), 136.0 (C), 136.5 (CH), 144.5 (C), 160.7 (CON), 176.2 (COO).

Example 3—Preparation of the Compound of Formula IV

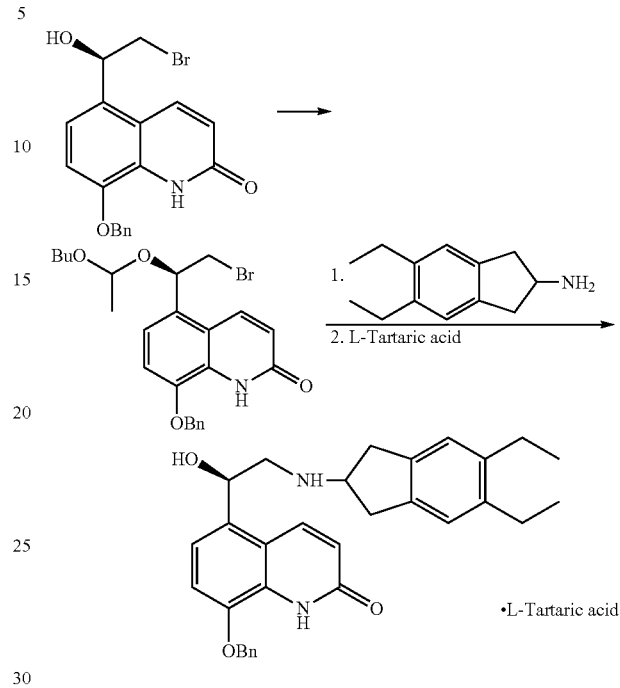

A flask was charged with 2.5 ml of THF and 2.5 ml of toluene. p-toluene sulfonic acid (5 mg) and molecular sieves (0.2 g) were added with stirring for 30 minutes. 1.5 ml of butyl-vinylether and 2 g of 8-(phenylmethoxy)-5-((R)-2-bromo-1-hydroxy-ethyl)-(1H)-quinolin-2-one were added. The mixture was agitated at 20/25° C. until completion of the reaction. 0.015 ml of diisopropylethyl amine was added, the mixture was filtered, and the solvent was distilled off.

The residue was dissolved in 6 ml of dimethylformamide (DMF), 1.9 ml of diisoproypylethyl amine, 1.2 g sodium iodide, and 1.5 g of 2-amino-5,6-diethylindane were added and the mixture was heated to 100° C. After completion of the reaction the mixture was cooled to 20/25° C., 0.4 ml of concentrated hydrochloric acid and 0.4 ml of water were added, and the mixture was stirred for 30 minutes.

HPLC analysis showed the expected product with a purity of 75% and being free from the dimer and regioisomer impurities.

20 ml of water, 20 ml of methylene chloride, and 3 ml of 6N NaOH were added with stirring. The organic phase was separated and washed with 20 ml of water. The organic phase was distilled and the solvent was changed to ethyl acetate with a final volume of 100 ml. The mixture was heated to 70° C., 0.8 g of L-tartaric acid was added, and stirring continued for 30 minutes at 70° C. The mixture was cooled slowly to 20/25° C., filtered, and washed with 8 ml of ethyl acetate to obtain 8-(phenylmethoxy)-5-[(R)-2-(5,6-diethyl-indan-2-ylamino)-1-hydroxy-ethyl]-(1H)-quinolin-2-one tartrate in 68% yield. The purity of the product was >95% by HPLC analysis.

Example 4—Preparation of the Compound of Formula IV

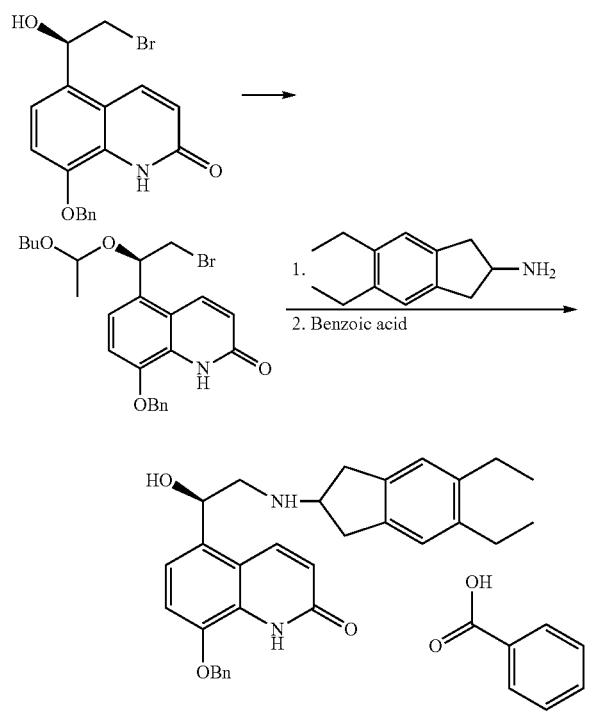

A flask was charged with 19 ml of THF and 19 ml of toluene. p-toluene sulfonic acid (75 mg) and molecular sieves (1.5 g) were added and the mixture was stirred for 30 minutes. 11.2 ml of butyl-vinylether and 15 g of 8-(phenylmethoxy)-5-((R)-2-bromo-1-hydroxy-ethyl)-(1H)-quinolin-2-one were added. The mixture was agitated at 20/25° C. until completion of the reaction. 0.1 ml of diisopropylethyl amine were added, the mixture was filtered, and the solvent was distilled off.

The residue was dissolved in 40 ml of butanone, 14.5 ml of diisoproypylethyl amine, 9 g sodium iodide, and 11.3 g of 2-amino-5,6-diethylindane were added and the mixture was heated to 90-100° C. After completion of the reaction the mixture was cooled to 20/25° C., 3 ml of concentrated hydrochloric acid and 3 ml of water were added, and the mixture was stirred for 30 minutes.

HPLC analysis showed the expected product with a purity of 84% and being free from the dimer and regioisomer impurities.

150 ml of water, 150 ml of methylene chloride, and 22.5 ml of 6N NaOH were added with stirring. The organic phase was separated and washed with 10 ml of water. The organic phase was distilled and the solvent was changed to isopropyl alcohol with a final volume of 300 ml. The mixture was heated to 70° C., 4.9 g of benzoic acid was added, and stirring continued for 30 minutes at 70° C. The mixture was cooled slowly to 20/25° C., filtered, and washed with 30 ml of isopropanol to obtain 8-(phenylmethoxy)-5-[(R)-2-(5,6-diethyl-indan-2-ylamino)-1-hydroxy-ethyl]-(1H)-quinolin-2-one benzoate in 59% yield. The purity of the product was >99% by HPLC analysis.

Example 5—Preparation of the Compound of Formula IV

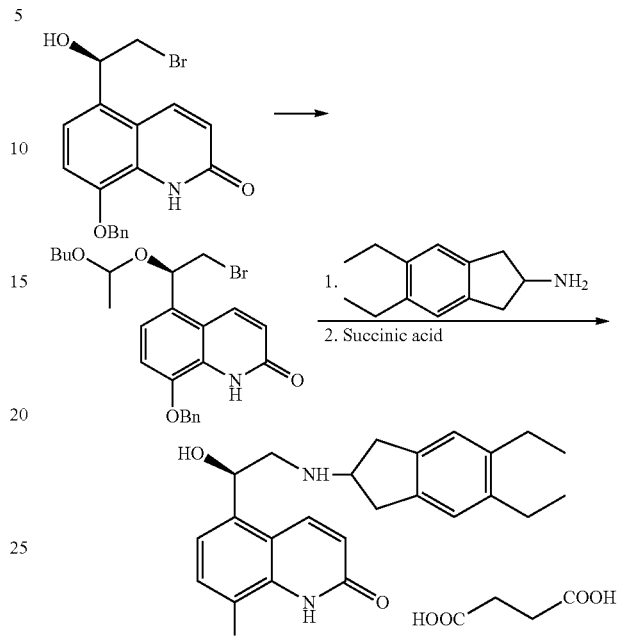

A flask was charged with 7.5 ml of THF and 7.5 ml of toluene. p-toluene sulfonic acid (30 mg) and molecular sieves (0.6 g) were added and the mixture was stirred for 30 minutes. 4.5 ml of butyl-vinylether and 6 g of 8-(phenylmethoxy)-5-((R)-2-bromo-1-hydroxy-ethyl)-(1H)-quinolin-2-one were added. The mixture was agitated at 20/25° C. until completion of the reaction. 0.040 ml of diisopropylethyl amine were added, the mixture was filtered, and the solvent was distilled off.

The residue was dissolved in 18 ml of acetonitrile (ACN), 5.8 ml of diisoproypylethyl amine, 3.6 g sodium iodide, and 4.5 g of 2-amino-5,6-diethylindane were added and the mixture was heated to 80-90° C. After completion of the reaction the mixture was cooled to 20/25° C., 1.2 ml of concentrated hydrochloric acid and 1.2 ml of water were added, and the mixture was stirred for 30 minutes. HPLC analysis showed the expected product with a purity of 89% and being free from the dimer and regioisomer impurities.

60 ml of water, 60 ml of methylene chloride, and 9 ml of 6N NaOH were added with stirring. The organic phase was separated and washed with 60 ml of water. The organic phase was distilled and the solvent was changed to isopropyl alcohol with a final volume of 120 ml. The mixture was heated to 70° C., 1.9 g of succinic acid was added, and stirring continued for 30 minutes at 70° C. The mixture was cooled slowly to 20/25° C., filtered, and washed with 12 ml of isopropanol to obtain 8-(phenylmethoxy)-5-[(R)-2-(5,6-diethyl-indan-2-ylamino)-1-hydroxy-ethyl]-(1H)-quinolin-2-one succinate in 56% yield. The purity of the product was >99% by HPLC analysis.

Example 6—Preparation of Indacaterol Maleate

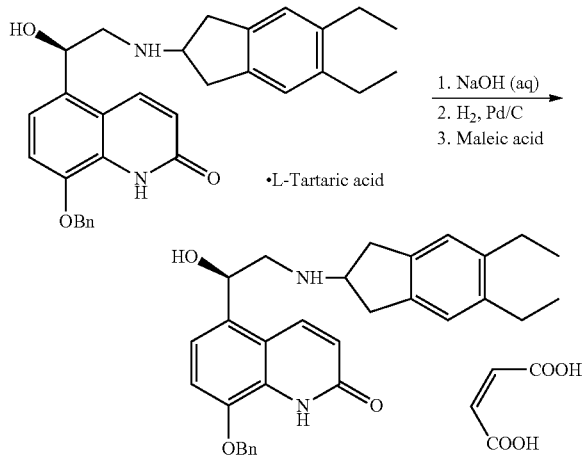

28 g of 8-(phenylmethoxy)-5-[(R)-2-(5,6-diethyl-indan-2-ylamino)-1-hydroxy-ethyl]-(1H)-quinolin-2-one tartrate was dissolved in a mixture of 560 ml of dichloromethane, 560 ml of water, and 30 ml of an aqueous solution of 6N sodium hydroxide under stirring. The phases were separated and the organic phase was washed with 280 ml of water.

The organic phase was distilled to a final volume of 140 ml and 420 ml of methanol and 4.2 g of Pd/C (5%-50% water) were added. The system was purged with nitrogen and subsequently with hydrogen at an overpressure of 0.3 bar and stirring until completion of the reaction.

The catalyst was filtered off and the solvent was changed to isopropanol adjusting the final volume to 950 ml. The solution was heated to 70/80° C. and a solution of 5.4 g maleic acid in 140 ml of isopropanol was added, maintaining the temperature between 70 and 80° C. The mixture was stirred at 70/80° C. for 30 minutes and then slowly cooled to 20/25° C. The resulting suspension was filtered, the solid residue was washed with 90 ml of isopropanol and dried to obtain 18 g of Indacaterol maleate (Yield: 79%). The product showed 99.6% purity by HPLC analysis.

Example 7—Isolation of Indacaterol Free Base in Solid Form

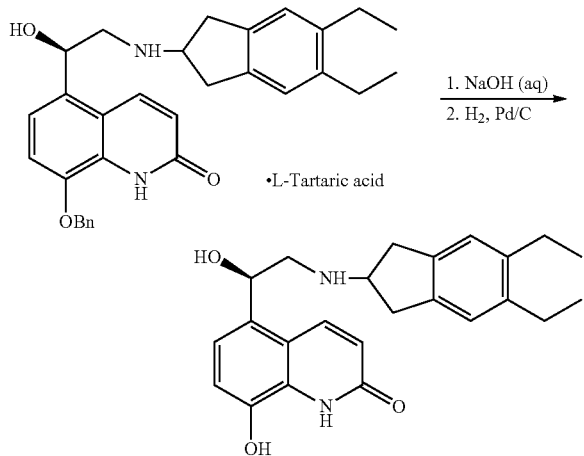

1 g of 8-(phenylmethoxy)-5-[(R)-2-(5,6-diethyl-indan-2-ylamino)-1-hydroxy-ethyl]-(1H)-quinolin-2-one tartrate was dissolved in a mixture of 20 ml of dichloromethane, 20 ml of water, and 1 ml of an aqueous solution of 6N sodium hydroxide under stirring. The phases were separated and the organic phase was washed with 10 ml of water.

The organic phase was distilled to a final volume of 5 ml and 15 ml of methanol and 0.15 g of Pd/C (5%-50% water) were added. The system was purged with nitrogen and subsequently with hydrogen at an overpressure of 0.3 bar and stirring until completion of the reaction.

The catalyst was filtered off and the solvent was changed to isopropanol adjusting the final volume to 8 ml. The resulting suspension was cooled to 0-5° C., filtered and the solid residue was washed with isopropanol and dried to obtain 0.47 g of Indacaterol free base (77%) showing 99.6% purity by HPLC analysis.

A sample of Indacaterol free base stored at 20-25° C. was analysed one month later without showing any loss of purity.

Example 8—Obtaining the Maleate Salt from Indacaterol Free Base

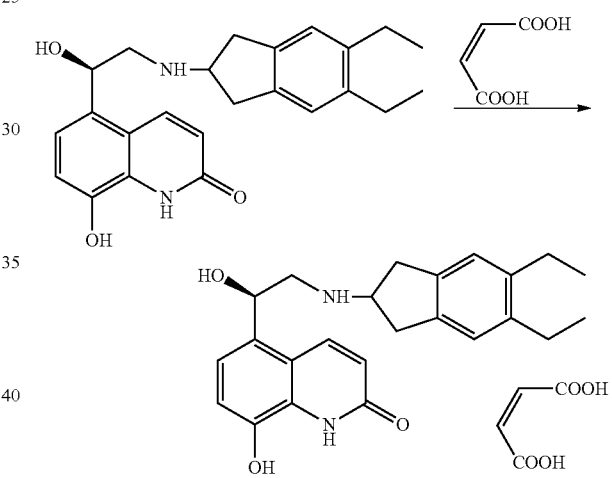

0.47 g of solid Indacaterol were suspended in 20 ml of isopropanol, heated to 70/80° C., and a solution of 0.15 g of maleic acid in 5 ml of isopropanol were added, maintaining the temperature between 70 and 80° C. The mixture was cooled to 0/5° C. and filtration of the resulting solid afforded 0.52 g of Indacaterol maleate with a purity of 99.7%.

Comparative Example 9—Direct Conversion to Indacaterol Maleate 8-(phenylmethoxy)-5-[(R)-2-(5,6-diethyl-indan-2-ylamino)-1-hydroxy-ethyl]-(1H)-quinolin-2-one benzoate (4 g) was dissolved in acetic acid (40 ml). Pd/C (5%, 50% wet, 0.6 g) was added and the product was hydrogenated under a hydrogen atmosphere. When the reaction was complete the catalyst was filtered off and the filtrate was vacuum distilled until a volume of 8 ml was reached.

Ethanol (40 ml) was added and the mixture was heated to 50° C. A solution of 1.2 g of maleic acid in 2.4 ml of ethanol was added and the mixture was seeded with indacaterol maleate and then slowly cooled to 0/5° C. The solid was filtered and washed with 5 ml of ethanol and 3 ml of isopropanol to obtain 6.0 g of indacaterol maleate.

1H-NMR analysis of the solid showed the presence of acetic acid in 2-4% by integration of the peak at δ 1.88 (400 MHz, DMSO-d6) corresponding to acetic acid.

The invention claimed is:

1. Indacaterol free base in solid form, wherein said Indacaterol free base is in crystalline form.

* * * * *